United States Patent
Haensler

Patent Number: 6,124,270
Date of Patent: *Sep. 26, 2000

[54] USE OF A CATIONIC AMPHIPATHIC COMPOUND AS A TRANSFECTION AGENT, VACCINE ADDITIVE OR DRUG

[75] Inventor: Jean Haensler, Saint-Genis-les-Ollières, France

[73] Assignee: Pasteur Merieux Serums et Vaccins, Lyons, France

[*] Notice: This patent issued on a continued prosecution application filed under 37 CFR 1.53(d), and is subject to the twenty year patent term provisions of 35 U.S.C. 154(a)(2).

[21] Appl. No.: 08/750,503

[22] PCT Filed: Apr. 11, 1996

[86] PCT No.: PCT/FR96/00547

§ 371 Date: Mar. 3, 1997

§ 102(e) Date: Mar. 3, 1997

[87] PCT Pub. No.: WO96/32102

PCT Pub. Date: Oct. 17, 1996

[30] Foreign Application Priority Data

Apr. 11, 1995 [FR] France ................... 95 04615

[51] Int. Cl.$^7$ .................... A61K 31/215; A61K 39/00
[52] U.S. Cl. ............... 514/44; 514/529; 560/250; 560/251; 560/252; 560/253; 560/261; 560/262; 560/263; 560/264; 560/265; 560/266; 424/812; 435/320.1
[58] Field of Search ................ 560/250, 251, 560/252, 253, 261, 262, 263, 264, 265, 266; 424/450, 812; 514/529, 44; 536/22.1; 435/320.1

[56] References Cited

U.S. PATENT DOCUMENTS

| | | | |
|---|---|---|---|
| 3,906,092 | 9/1975 | Hilleman et al. | 424/89 |
| 4,897,355 | 1/1990 | Eppstein et al. | 435/240.2 |
| 5,283,185 | 2/1994 | Epand et al. | 435/172.3 |
| 5,641,662 | 6/1997 | Debs et al. | 435/172.1 |
| 5,736,524 | 4/1998 | Content et al. | 514/44 |

FOREIGN PATENT DOCUMENTS

WO93/12756 7/1993 WIPO.
WO96/05218 2/1996 WIPO.

OTHER PUBLICATIONS

Kunitake et al., "Bilayer Membranes . . . Amphipiles", J. Am. Chem. Soc., vol. 106, pp. 1978–1983, 1984.
Felgner et al., "Enhanced Gene . . . Formulations", J. of Biol. Chem., vol. 269, No. 4, pp. 2550–2561, Jan. 1994.
T. Kunitake et al., "Bilayer Membranes of Triple–Chain Ammonium Amphiphiles" J.Am.Chem.Soc. (1984) 106:1978–1983.

Primary Examiner—Gary Geist
Assistant Examiner—Rosalynd Keys
Attorney, Agent, or Firm—Burns, Doane, Swecker & Mathis, L.L.P.

[57] ABSTRACT

A cationic amphipathic compound of formula (I),

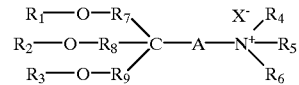

wherein A is a single bond, an NH—R' grouping or (a), wherein —R'— is a straight or branched, optionally substituted, saturated or unsaturated $C_{1-22}$ aliphatic chain optionally interrupted by one or more O, S or N heteroatoms and one or more saturated, unsaturated or aromatic carbocyclic or heterocyclic radicals; each of $R_1$, $R_2$ and $R_3$, which are the same or different, is a higher acyl or alkyl grouping; each of $R_7$, $R_8$ and $R_9$, which are the same or different, is a $(CH_2)_n$ alkylene radical where $1 \leq N \leq 6$; each of $R_4$, $R_5$ and $R_6$, which are the same or different, is a hydrogen atom or an optionally substituted $C_{1-22}$ alkyl, alkenyl, alkynyl or acyl radical optionally interrupted by one or more heteroatoms selected from), S and N, or one or more saturated, unsaturated or aromatic carbocyclic or heterocyclic radicals, or else at least two of the groupings $R_4$, $R_5$ and $R_6$, taken together with the nitrogen atom to which they are attached, form a quinuclidino, piperidino, pyrrolidino or morpholino grouping, and X is a non-toxic anion. For use as a drug, a transfection agent or an additive in a vaccine composition.

17 Claims, 5 Drawing Sheets

USE OF A CATIONIC AMPHIPATHIC COMPOUND AS A TRANSFECTION AGENT, VACCINE ADDITIVE OR DRUG

This is a national stage application of PCT/FR96/00547, filed on Apr. 11, 1996, which designated the United States.

The invention relates to the field of cationic amphipathic compounds and to their use in particular as transfection agent or as vaccine additive.

Transfection, that is to say the introduction, without damage, into a living eukaryotic cell of DNA or mRNA (messenger RNA) capable of being expressed, constitutes an alternative approach to the intracellular introduction of polypeptides and proteins. This technique finds application in numerous fields ranging from cell biology to therapy. In cell biology, transfection techniques can be used especially to study the intracellular role of cloned gene products and to study the regulation of gene expression. Transfection is also used in gene therapy for the correction of genetic disorders; it also finds application in the field of therapeutic peptides and in immunization with the development of polynucleotide vaccines.

There are known in the prior art numerous transfection methods, of which in particular precipitation of DNA and calcium phosphate or DEAE-dextran, or alternatively the use of cationic lipids in the form of liposomes which form complexes with negatively charged polynucleotides and facilitate their transmembrane passage. Among the cationic lipids known, there may be mentioned:

DOTMA (or N-[1-(2,3-dioleyloxy)propyl]-N,N,N-trimethylammonium chloride) marketed in combination with a neutral lipid, DOPE (or dioleoylphosphatidyl-ethanolamine) in the form of liposomes, by the company GIBCO BRL under the name Lipofectin™, lipospermines, such as DOGS (5-carboxyspermyl-glycine-dioctadecylamide) supplied by the company SEPRACOR under the name Transfectam™, and DOSPA (2,3-dioleyloxy-N-[2-(sperminecarboxamido) ethyl]-N,N-dimethyl-propaneammonium trifluoroacetate) supplied by the company GIBCO BRL under the name Lipofectamine™, lipopolylysines (Cf. Zhou et al, Biochim. Biophys. Acta, 1065, 8–14, 1991), quaternary ammonium detergents such as cetyltrimethylammonium or DDAB (dimethyldioctadecylammonium bromide) marketed in combination with a neutral lipid in the form of liposomes by the company GIBCO BRL under the name Transfectace™, cationic derivatives of cholesterol such as DC chol (3β-[N-(N'N'-dimethylaminoethane)carbamoyl]-cholesterol) (Cf. X. Gao and L. Huang, Biochem. Biophys. Res. Commun., 1979, 280–285, 1991), metabolizable analogues of DOTMA such as DOTAP(1, 2-dioleyloxy-3-(trimethylammonio)propane) supplied by the company BOEHRINGER MANNHEIM.

Although a number of these products are commercially available and are effective for the transfection of cells in culture, their efficacy in vivo is limited. The need therefore exists for new transfection agents capable of promoting the passage of polynucleotides across the negatively charged cell membrane, which are not or not very toxic and which are effective in vivo.

The aim of the invention is to provide such transfection agents having fusogenic properties with the cell membrane or the endosome membrane.

To achieve this aim, the subject of the invention is a cationic amphipathic compound of formula I:

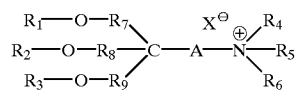

in which:
A represents a single bond, an NH—R' group, or an

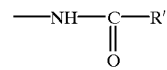

group, where —R'— is an aliphatic chain containing from 1 to 22 carbon atoms, which is linear or branched, optionally substituted, saturated or unsaturated, optionally interrupted by one or more heteroatoms O, S, N, as well as by one or more aromatic or saturated or unsaturated heterocyclic or carbocyclic radicals, $R_1$, $R_2$, $R_3$ are identical or different and each represent a higher alkyl or acyl group, $R_7$, $R_8$, $R_9$ are identical or different and each represent an alkylene radical —$(CH_2)_n$— where $1 \leq n \leq 6$, $R_4$, $R_5$, $R_6$ are identical or different and each represent:
a hydrogen atom,
an alkyl, alkenyl, alkynyl or acyl radical containing from 1 to 22 carbon atoms, which is optionally substituted, optionally interrupted by one or more heteroatoms chosen from O, S, N or by one or more aromatic or saturated or unsaturated heterocyclic or carbocyclic radicals,
or alternatively, at least 2 of the groups $R_4$, $R_5$ and $R_6$ form together with the nitrogen atom to which they are linked a quinuclidino, piperidino, pyrrolidino or morpholino group,
X is a nontoxic anion, for use as a drug.

According to one specific characteristic of the invention, $R_7$, $R_8$ and $R_9$ are all identical and represent the methylene group —$CH_2$—.

According to another characteristic of the invention, $R_4$, $R_5$ and $R_6$ are all identical and represent the methyl group $CH_3$—.

According to another characteristic, $R_1$, $R_2$ and $R_3$ are all identical and represent a higher acyl group such as dodecanoyl or hexadecanoyl.

According to another characteristic, A represents a group

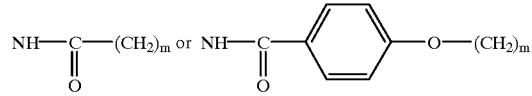

where $1 \leq m \leq 22$,

According to a specific mode of the invention, the cationic amphipathic compound of formula I is combined with a neutral lipid, such as dioleoylphosphatidylethanolamine, in a molar ratio of between 9/1 and 1/9.

The subject of the invention is also the compound of formula I for use as transfection agent.

The subject of the present invention is also a method of transfection of eukaryotic cells, characterized in that it consists in mixing the compound of formula I with at least one plasmid or one polynucleotide, and in bringing the mixture thus obtained into contact with cells to be transfected.

The subject of the invention is also a transfection agent characterized in that it comprises at least one compound of formula I.

According to a specific embodiment, the transfection agent is provided in the form of liposomes which may be in aqueous suspension or freeze-dried.

The subject of the invention is also a pharmaceutical composition characterized in that it comprises at least one compound of formula I.

The subject of the invention is, in addition, the compound of formula I for use as adjuvant in a vaccine composition.

The subject of the invention is also a vaccine composition characterized in that it comprises at least one compound of formula I.

The subject of the invention is furthermore the use of a cationic amphipathic compound of formula I for the manufacture of a drug which can be used in gene therapy.

The subject of the invention is further the use of a cationic amphipathic compound of formula I for the manufacture of a drug which can be used in vaccination.

The present invention will be understood more clearly on reading the description and the examples which follow with reference to the figures which illustrate the results of a number of trials carried out.

Figure 1:
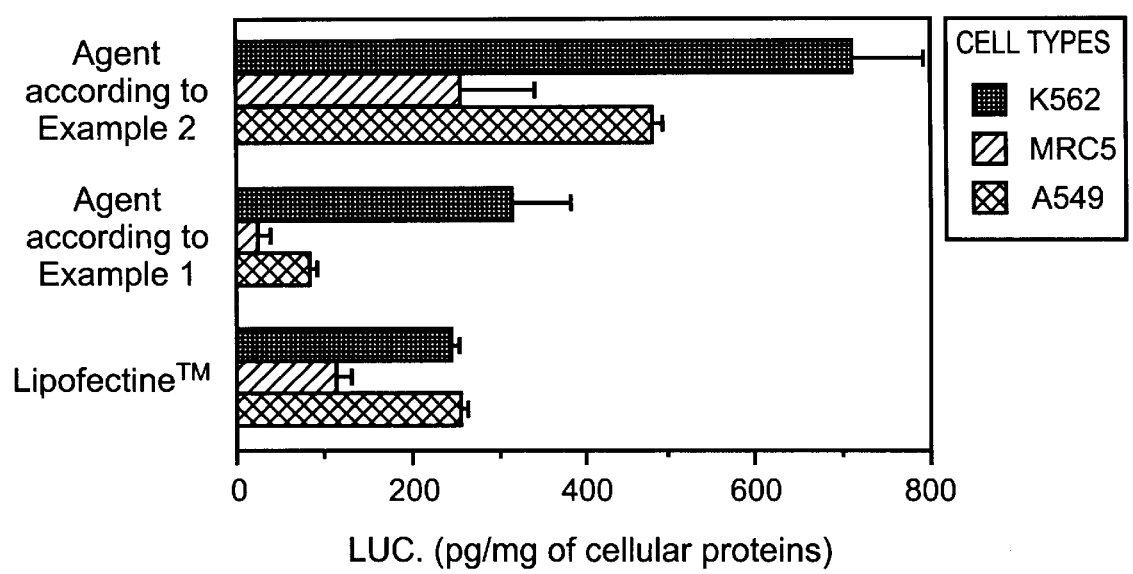
FIG. 1 illustrates the results obtained in Example 4, that is to say the activity of luciferase in pg/mg of cellular proteins for the transfection agent obtained according to Example 1, the transfection agent obtained according to Example 2 and a transfection agent of the prior art.

For the purposes of the present invention, polynucleotide is understood to mean any molecule consisting of a succession of nucleotides, such as DNA, RNA or triple helix.

Alkyl radical is understood to mean any hydrocarbon radical preferably having from 1 to 32 carbon atoms and containing only single bonds. Lower alkyl radical is understood to mean a radical comprising from 1 to 10 carbon atoms; it may, in particular, be a methyl, ethyl, propyl, isopropyl, butyl, isobutyl, n-pentyl, n-hexyl, 2-methylpentyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl, n-nonyl or n-decyl radical. Higher alkyl radical is understood to mean a radical comprising more than 10 carbon atoms; it may, in particular, be undecyl, dodecyl, tridecyl, tetradecyl, pentadecyl, hexadecyl, heptadecyl, octadecyl, nonadecyl, eicosyl, heneicosyl, docosyl or triacontyl radicals.

Alkenyl radical is understood to mean any hydrocarbon radical containing at least one double bond but no triple bond. The alkenyl radicals according to the invention preferably possess from 2 to 32 carbon atoms. Lower alkenyl radical is understood to mean a radical having from 2 to 10 carbon atoms such as a vinyl, allyl, propenyl, isopropenyl, 2-methylallyl, butenyl or isobutenyl radical. Higher alkenyl radical is understood to mean a radical having more than 10 carbon atoms.

Alkynyl radical is understood to mean any hydrocarbon radical containing at least one triple bond. The alkynyl radicals according to the invention preferably contain from 2 to 32 carbon atoms. Lower alkynyl radical is understood to mean a radical having from 2 to 10 carbon atoms, such as an ethynyl, propynyl, propargyl, butynyl or isobutynyl radical. Higher alkynyl radical is understood to mean a radical having more than 10 carbon atoms.

Acyl radical is understood to mean a radical

where R is an alkyl, alkenyl or alkynyl radical as defined above. Lower acyl radical is understood to mean a radical

in which R contains at most 10 carbon atoms, and higher acyl radical is understood to mean a radical in which R contains more than 10 carbon atoms, such as the acyl radicals derived from the following acids: lauric, myristic, palmitic, stearic, arachidic, behenic, lignoceric and cerotic acid.

The following radicals are preferably used: dodecanoyl and hexadecanoyl derived from lauric acid and palmitic acid respectively.

Saturated carbocyclic radical is understood to mean, for example, a cyclopropyl, cyclobutyl, cyclopentyl or cyclohexyl radical.

Unsaturated carbocyclic radical is understood to mean, for example, a cyclobutenyl, cyclopentenyl, cyclopentadienyl, cyclohexenyl or cyclohexadienyl radical.

Saturated heterocyclic radical is understood to mean, for example, a pyrrolidinyl, piperidinyl, imidazolidinyl, pyrazolidinyl, piperazinyl, morpholinyl, thiomorpholinyl or azepinyl radical.

Aromatic, carbocyclic or heterocyclic radical is understood to mean for example a phenyl, thienyl, furyl, pyrranyl, pyrrolyl, imidazolyl, pyrazolyl, pyridyl, pyrazinyl, pyrimidinyl, pyridazinyl, thiazolyl, oxazolyl, furazanyl, pyrrolinyl, imidazo-linyl, pyrazolinyl, thiazolinyl, triazolyl, tetrazolyl, cyclopropanyl, cyclobutanyl, cyclopentanyl, cyclo-hexanyl, cycloheptanyl or cyclooctanyl and the like.

The expression "optionally substituted" applied to the aliphatic chain R' and to the alkyl, alkenyl, alkynyl or acyl radicals which $R_4$, $R_5$ and $R_6$ may represent indicates that the latter may be optionally substituted with one or more identical or different radicals chosen especially from the following radicals:

halogen: fluorine, chlorine, bromine, iodine, amino, alkylamino such as methylamino or ethylamino, dialkylamino such as dimethylamino, diethylamino, methylethylamino, optionally acylated hydroxyl, for example acetoxy, esterified carboxyl such as alkoxycarbonyl, for example methoxycarbonyl or ethoxycarbonyl, oxo, cyano, nitro, formyl, acyl such as acetyl, propionyl, butyryl, benzoyl, acyloxy such as acetoxy, alkoxy such as methoxy, ethoxy, propyloxy, isopropyloxy, butyloxy, alkylthio such as methylthio, ethylthio, propylthio, isopropylthio, butylthio, carbamoyl, The amphipathic compounds according to the invention are salts whose anion should be a pharmaceutically nontoxic anion obtained from organic or inorganic acids. Among these acids, there may be mentioned in particular hydrochloric acid, hydrobromic acid, sulphuric acid, phosphoric acid, acetic acid, benzoic acid, citric acid, glutamic acid and lactic acid. For the preparation of pharmaceutically acceptable salts, reference may be made to the publication by Berge S. M. et al. J. Pharm. Sci. 66:1–19 (1977). Specifically, hydrobromic acid salts are used.

The cationic amphipathic compounds suitable for the purposes of the invention may be obtained by any conventional method of acylation or alkylation of amino alcohols; there may be used, for example, the methods described in "Advanced Organic Chemistry" Part B: Reactions and Synthesis (F. A. Carey and R. J. Sundberg-Plenum Publishing Corp.). The starting amino alcohol compound may be hydroxymethylhydroxyethylhydroxypropylaminomethane, di (hydroxymethyl) hydroxyethylaminomethane, di(hydroxyethyl)hydroxymethylaminomethane, tris (hydroxymethyl)aminomethane or a higher homologue such as tris (hydroxyethyl) aminomethane, tris (hydroxypropyl) aminomethane, tris(hydroxybutyl)aminomethane, tris (hydroxypentyl) aminomethane or tris (hydroxyhexyl) aminomethane. Advantageously, tris (hydroxymethyl) aminomethane is used as starting compound.

The group which constitutes the cationic head of the amphipathic compound according to the invention may be generated by direct alkylation of the amino group of the starting amino alcohol compound (in this case, A, indicated in the general formula mentioned above, represents the single bond existing between the carbon atom C and the nitrogen atom N). Preferably, the cationic head is linked to the nitrogenous group via a spacer arm A, by alkylation or acylation carried out by means of an alkylating reagent (alkyl halide) or an acylating agent (activated carboxylic acid) which is positively charged or which can be modified so as to confer a positive charge on it.

The lipophilic portion of the amphipathic compounds suitable for the present invention consists of 3 hydrocarbon chains $R_1$, $R_2$, $R_3$ which are identical or different. These 3 chains are derived either from activated fatty alcohols, or from activated fatty acids which have reacted with the alcohol functional group of the starting amino alcohol compound to form an ether or ester bond respectively. Specifically, compounds obtained from dodecanoic acid or from hexadecanoic acid are used.

Among the compounds suitable for the purposes of the invention, there may be mentioned especially the compounds whose formula is the following:

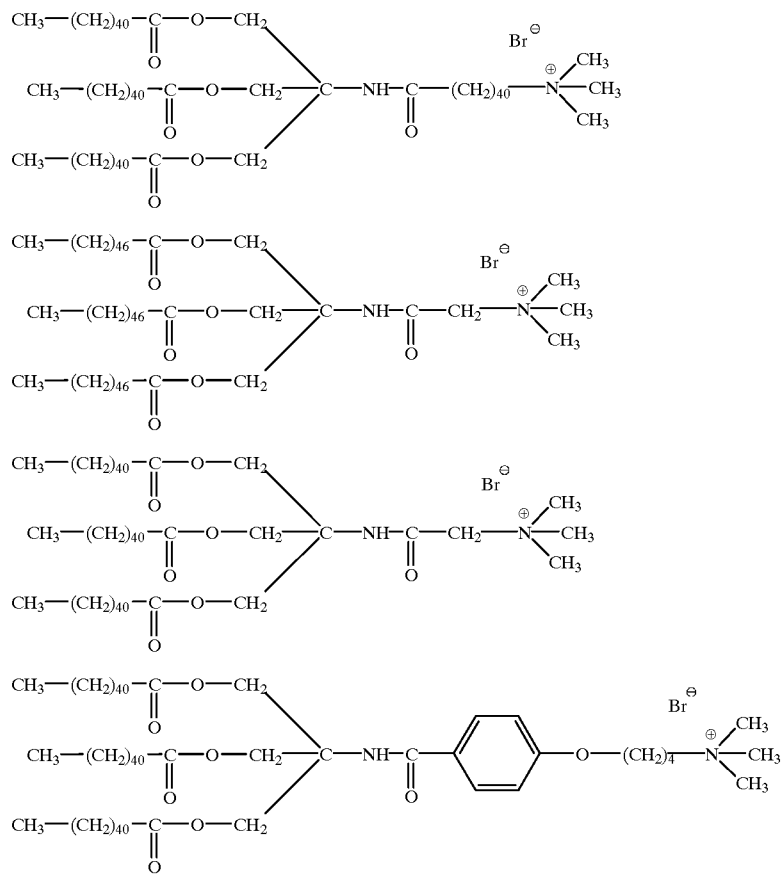

-continued

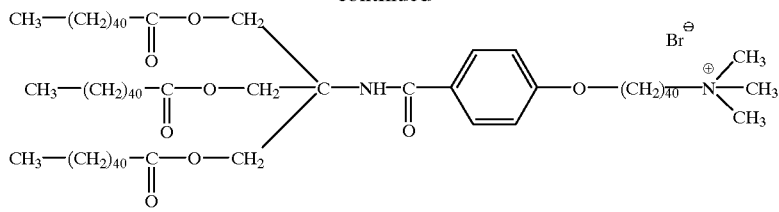

of which the method of manufacture is described in the article "Bilayer Membranes of Triple-Chain Ammonium Amphiphiles" Kunitake et al. J. Am. Chem. Soc. 1984, 106, 1978–1983.

According to one embodiment of the invention, the cationic amphipathic compound is combined with at least one neutral lipid, such as cholesterol, a phosphatidylcholine or a phosphatidylethanolamine. Particularly good results have been obtained by combining the cationic amphipathic compounds with dioleoylphosphatidylethanolamine (DOPE). The molar proportion of cationic amphipathic compound and neutral lipid is advantageously between 9/1 and 1/9. Specifically, a 1/2 ratio is used.

Subsequently, for the sake of simplicity, reference will be made to lipid formulation according to the invention to mean either the cationic amphipathic compound alone, or the cationic amphipathic compound combined with at least one neutral lipid, such as dioleoylphosphatidylethanolamine.

According to one embodiment, the lipid formulation of the present invention is organized in the form of liposomes with a single or multiple wall. These liposomes are obtained during the dispersion of the lipid formulation in aqueous medium. To obtain liposomes of uniform size, the lipid formulation according to the invention may be treated by any method known for this purpose by persons skilled in the art and published in the literature (e.g.: Liposomes: A practical Approach RRC New Ed. IRL Press, Oxford University Press, 1990). It is especially possible to rapidly inject into an aqueous medium an ethanolic solution of lipid formulations or to sonicate liposomes spontaneously formed from the lipid formulations in aqueous medium.

According to the invention, when the compound of formula I is intended to be used as transfection agent, the lipid formulations are combined with polynucleotides which it is desired to introduce in the cells, to form complexes by interaction of charges. This combination may be achieved simply by mixing the different compounds in solution.

The transfection agent according to the invention makes it possible to transfect numerous cells: it is possible, for example, to transfect adhering cell lines (e.g.: CHO-K1, A549), primary cells (e.g. MRC-5) and cell lines in suspension (e.g.: K562).

It has been possible to achieve transfection levels as high as 50 per cent with CHO cells.

By virtue of the transfection agent according to the invention, high quantities of plasmid DNA (up to 60 μg) can be transfected in a final volume of 100 μl; this result is important for an application in gene therapy where it is necessary to deliver a large quantity of polynucleotides in a volume compatible with a parenteral or mucosal administration.

The compound according to the invention may also be used as adjuvant in vaccine compositions in order to modify the immune response. In this case, it is possible to obtain a vaccine composition simply by mixing vaccinal antigens and liposomes or by encapsulation of the Ag's by liposomes, the liposomes being obtained from a lipid formulation according to the invention as has just been described.

The use of the compound according to the invention as transfection agent or as vaccine adjuvant has not caused any sign of toxicity. Indeed, observation under a microscope of transfected cells revealed no sign of cytotoxicity. In addition, during the in vivo transfer of genes in the mouse trachea and lungs, as well as during trials of immunization of mice by the subcutaneous route, no sign of acute toxicity appeared.

The following examples illustrate some embodiments of the invention, with no limitation being implied.

EXAMPLE 1

O, O', O"-tridodecanoyl-N-(ω-trimethylammoniododecanoyl)-tris-(hydroxymethyl) aminomethane bromide supplied by SOGO under the name TC-1-12 is available. 21 mg of it are dissolved in 75 μl of ethanol. 50 μl of this ethanolic solution (that is to say 15 μmol) are then rapidly injected with the aid of a Hamilton syringe into 2 ml of deionized water, with stirring, at 45° C. Small unilamellar vesicles of cationic amphipathic compound whose mean diameter is 50 nm are obtained under these conditions.

EXAMPLE 2

1.4 mg (that is to say 1.5 μmol) of O, O', O"-tridodecanoyl-N-(ω-trimethylammoniododecanoyl)-tris-(hydroxymethyl)aminomethane bromide and 2.24 mg (that is to say 3 μmol) of dioleoylphosphatidylethanolamine (DOPE) are mixed in chloroform and the mixture is dried on the walls of a glass vessel in a rotary evaporator; the lipid mixture is resuspended in 2 ml of sterile deionized water. After rehydration overnight at 4° C., the dispersion is sonicated for 10 min in order to form small unilamellar liposomes whose mean diameter is 100 to 200 nm.

EXAMPLE 3

The liposome suspensions obtained according to Example 1 or Example 2 are diluted in deionized water so as to have a concentration of 0.747 mM of positive charges and are used to transfect CHO cells in culture according to the method described by Felgner J. et al. J. Tiss. Cult. Meth., 15: 63–68, 1993.

The CHO cells are cultured in a 96-well plate (10 to 30,000 cells per well) one day before the transfection trial.

Liposome-DNA complexes having various quantities of DNA and of liposomes are prepared in the following manner:

1) Dilution of the Lipid Formulation

66 μl of αMEM medium are distributed into each well of the 1st column of a 96-well plate (that is to say wells $A_1$ to $H_1$) and 60 μl are distributed into all the other wells. 54 μl of the solution at 0.747 mM of positive charges of the lipid formulation obtained according to Example 1 or Example 2 are placed in each well of the 1st column. A serial dilution of the lipid solution is then carried out by transferring 60 µl from each well of column 1 to the corresponding well of column 2, and then 60 µl from each well of column 2 to the corresponding well of column 3, and so on up to column 8 (wells $A_8$–$H_8$).

2) Dilution of the Plasmid

The plasmid with which it is desired to transfect the cells is the plasmid pCMV-βGal which, when transfection occurs, will cause the cell to produce an enzyme, β-Galactosidase, whose activity can be easily measured. Various dilutions of the plasmid solution are made, again by virtue of a 96-well plate each containing 70 µl of αMEM medium. 70 µl of a plasmid solution containing 80 µg of pCMV-βGal/ml of αMEM medium are placed in each well of the first row (wells $A_1$–$A_8$). The plasmid solution is then serially diluted by transferring 70 µl of the plasmid solution from each well of the first row to the corresponding well of the second row, and then 70 µl of the solution from each well of the second row to the corresponding well of the third row and so on up to the eighth row (wells $H_1$–$H_8$).

The liposome/DNA complexes corresponding to various quantities of DNA and to various values of the liposome charge are obtained by transferring 60 µfrom each well of the plate containing the plasmids to the corresponding well of the plate containing the liposomes. After incubating for 10 minutes at room temperature, 100 µl of the resulting complexes are transferred onto the cell layers. The cells are incubated at 37° C. in a humid atmosphere comprising 5% $CO_2$. Serum is added to the cultures 5 hours after the transfection (by addition of 50 µl of αMEM containing 30% foetal calf serum) as well as 24 h after the transfection (addition this time of 100 µl of αMEM containing 10% foetal calf serum).

The transfection efficiency is measured at 48 hours after lysis of the cells, using ONPG (orthonitrophenylgalactoside) as substrate to detect and measure, according to a calorimetric method, the β-galactosidase activity produced by the cells. β-galactosidase converts the colourless ONPG to galactose and to the yellow-coloured ortho-nitrophenol (absorption at 405 nm).

The results obtained are represented in the tables below where the optical density read at 405 nm is indicated for each well.

For each table, the wells of the 9th column correspond to negative controls representing the background noise, whereas the wells of the 10th column are used to prepare a β-galactosidase calibration series; the 1st well of the tenth column corresponds to a concentration of 400 ng/ml, the 2nd to 200 ng/ml, the 3rd to 100 ng/ml, and so on at concentrations reduced each time by half, up to the 8th well where the concentration is 3.125 ng/ml.

Table 1 indicates the results obtained with the liposomes of Example 1.

TABLE 1

|   | 1 | 2 | 3 | 4 | 5 | 6 | 7 | 8 | 9 | 10 |
|---|---|---|---|---|---|---|---|---|---|---|
| A<br>2 µg DNA | 2.456 | 3.317 | 3.446 | 3.300 | 1.265 | 0.396 | 0.230 | 0.152 | 0.131 | 3.259 |
| B<br>1 µg DNA | 0.876 | 3.281 | 3.289 | 3.551 | 1.417 | 0.362 | 0.190 | 0.145 | 0.146 | 3.299 |
| C<br>0.5 µg DNA | 0.255 | 1.027 | 3.581 | 3.438 | 2.331 | 0.583 | 0.315 | 0.141 | 0.127 | 2.383 |
| D<br>0.25 µg DNA | 0.185 | 0.404 | 3.247 | 3.050 | 2.586 | 0.639 | 0.216 | 0.137 | 0.129 | 1.289 |
| E<br>0.125 µg DNA | 0.167 | 0.256 | 1.736 | 2.145 | 2.422 | 0.490 | 0.169 | 0.139 | 0.135 | 0.745 |
| F<br>0.062 µg DNA | 0.174 | 0.248 | 0.829 | 0.799 | 0.691 | 0.296 | 0.151 | 0.132 | 0.131 | 0.472 |
| G<br>0.031 µg DNA | 0.173 | 0.184 | 0.536 | 0.319 | 0.388 | 0.333 | 0.146 | 0.140 | 0.140 | 0.364 |
| H<br>0.015 µg DNA | 0.169 | 0.185 | 0.377 | 0.270 | 0.201 | 0.210 | 0.216 | 0.144 | 0.155 | 0.257 |
| No. of nmoles of + charges | 17 | 8.5 | 4.25 | 2.13 | 1.06 | 0.53 | 0.27 | 0.13 | | |

Table 2 indicates the results obtained with the liposomes of Example 2.

TABLE 2

|   | 1 | 2 | 3 | 4 | 5 | 6 | 7 | 8 | 9 | 10 |
|---|---|---|---|---|---|---|---|---|---|---|
| A<br>2 µg DNA | 1.205 | 1.819 | 2.821 | 2.452 | 2.349 | 2.322 | 1.688 | 1.115 | 0.121 | 3.347 |
| B<br>1 µg DNA | 0.467 | 1.225 | 2.460 | 2.448 | 2.362 | 2.479 | 2.302 | 1.377 | 0.118 | 3.283 |
| C<br>0.5 µg DNA | 0.459 | 1.004 | 2.090 | 2.547 | 2.175 | 2.307 | 2.187 | 1.599 | 0.116 | 2.194 |
| D<br>0.25 µg DNA | 0.363 | 0.958 | 1.892 | 2.001 | 2.467 | 2.397 | 2.405 | 1.659 | 0.119 | 1.168 |
| E<br>0.125 µg DNA | 0.273 | 0.795 | 1.592 | 2.318 | 2.267 | 2.405 | 2.085 | 1.488 | 0.122 | 0.667 |
| F<br>0.062 µg DNA | 0.275 | 0.578 | 1.188 | 1.746 | 2.084 | 2.435 | 1.905 | 1.403 | 0.121 | 0.430 |

TABLE 2-continued

|   | 1 | 2 | 3 | 4 | 5 | 6 | 7 | 8 | 9 | 10 |
|---|---|---|---|---|---|---|---|---|---|----|
| G<br>0.031 μg DNA | 0.175 | 0.402 | 0.915 | 1.106 | 1.682 | 1.915 | 1.330 | 0.911 | 0.124 | 0.336 |
| H<br>0.015 μg DNA | 0.166 | 0.233 | 0.556 | 0.585 | 0.892 | 1.209 | 1.040 | 0.546 | 0.139 | 0.236 |
| No of nmoles of + charges | 17 | 8.5 | 4.25 | 2.13 | 1.06 | 0.53 | 0.27 | 0.13 | | |

Table 3 indicates the results obtained with a transfection agent of the prior art: DOTMA marketed under the name Lipofectin™.

TABLE 3

|   | 1 | 2 | 3 | 4 | 5 | 6 | 7 | 8 | 9 | 10 |
|---|---|---|---|---|---|---|---|---|---|----|
| A<br>2 μg DNA | 0.322 | 0.747 | 3.189 | 3.124 | 3.283 | 2.619 | 1.883 | 1.350 | 0.133 | 3.289 |
| B<br>1 μg DNA | 0.234 | 0.334 | 1.594 | 3.454 | 3.256 | 3.141 | 2.362 | 1.423 | 0.138 | 3.249 |
| C<br>0.5 μg DNA | 0.200 | 0.205 | 1.060 | 2.977 | 3.549 | 3.043 | 2.288 | 1.099 | 0.130 | 2.585 |
| D<br>0.25 μg DNA | 0.190 | 0.170 | 0.666 | 1.802 | 3.099 | 3.397 | 1.866 | 1.073 | 0.129 | 1.506 |
| E<br>0.125 μg DNA | 0.173 | 0.143 | 0.289 | 0.758 | 2.022 | 3.443 | 1.635 | 0.619 | 0.125 | 0.855 |
| F<br>0062 μg DNA | 0.170 | 0.139 | 0.158 | 0.371 | 0.733 | 1.449 | 1.595 | 0.585 | 0.129 | 0.565 |
| G<br>0.031 μg DNA | 0.167 | 0.138 | 0.136 | 0.223 | 0.334 | 0.513 | 0.615 | 0.294 | 0.131 | 0.392 |
| H<br>0.015 μg DNA | 0.169 | 0.135 | 0.139 | 0.171 | 0.216 | 0.302 | 0.318 | 0.254 | 0.141 | 0.334 |
| No. of nmoles of + charges | 17 | 8.5 | 4.25 | 2.13 | 1.06 | 0.53 | 0.27 | 0.13 | | |

The results obtained show the efficiency of the transfection performed either with liposomes consisting solely of the cationic amphipathic compound according to the invention or with liposomes consisting both of the cationic amphiphathic compound according to the invention and of a neutral colipid.

EXAMPLE 4

The efficiency of the transfection performed with the lipid formulations according to the invention and with an agent of the prior art is evaluated on various types of cells: the A 549 cells (human lung carcinoma epithelial cell lines), the MRC5 cells (human foetal pulmonary fibroblasts) and on a cell line in suspension, the K 562 cells (lymphoblasts derived from a myelogenous human chronic leukaemia).

The cells are transfected, this time, with the plasmid pCMV-Luc which, when expressed, leads to the production, by the cells, of an enzyme: luciferase, whose activity can be assayed using, as substrate, luciferin, according to the technique described in the article "Firefly Luciferase Gene Structure and Expression in Mammalian Cells." (J. R. De Wet et al., Mol. Cell Biol., 7, 725–737, 1987).

The adherent cells are spread a day before the transfection assay in 60 mm Petri dishes at a density allowing them to reach a confluency of ½–¾ at the time of the transfection. Plasmid/transfection agent complexes are prepared by adding 5 μg of plasmid in suspension in an appropriate culture medium containing serum (αMEM medium for MRC5 cells, DMEM medium for A 549 cells, and RPMI 1640 medium for K 562 cells) to 0.5 ml of the same medium containing a quantity of liposomes which make it possible to obtain a + charge/− charge ratio of 0.7 for Lipofectin™ as well as for the transfection agent obtained according to Example 2, and a ratio equal to 1.4 for the transfection agent obtained according to Example 1. After mixing and incubating for 10 minutes at room temperature, the resulting complexes are added to the cells and incubated at 37° C. in a humid atmosphere containing 5% $CO_2$.

Serum is added to the cultures 5 hours after the transfection (by addition of 0.5 ml of the appropriate medium containing 30% foetal calf serum) and 24 hours after the transfection (by addition, this time, of 1 ml of the appropriate medium containing 10% foetal calf serum). The transfection efficiency is evaluated at 48 hours, using luciferin as substrate according to the technique mentioned above.

To transfect cells in suspension, plasmid pCMV-Luc/lipid formulation complexes are prepared from RPMI 1640 medium as described above. The solution obtained is then used to resuspend 1.5×10 K 562 cells in 35 mm Petri dishes. Dilute serum is added and the transfection is evaluated as described above for the adherent cells.

The results obtained are represented on the histogram of FIG. 1, where it can be seen that it was possible to transfect all the cell types.

EXAMPLE 5

CHO cells are transfected with concentrated DNA/lipid formulation complexes.

Figure 2:
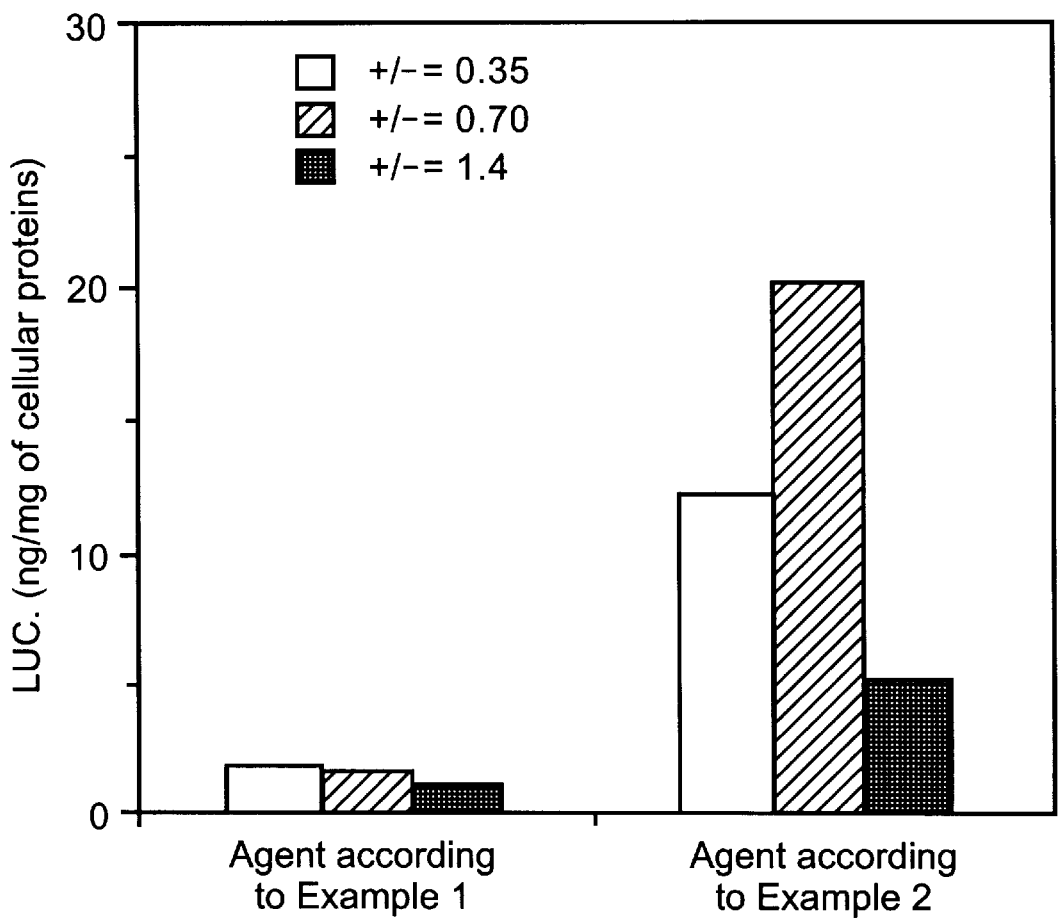
FIG. 2 illustrates the results obtained in Example 5.

Complexes are prepared by adding a suspension of lipid formulation in 50 μl of deionized water to a solution containing 60 μg of plasmid pCMV-Luc in 50 μl of physiological saline. The quantity of lipids is adjusted to obtain + charge/− charge ratios of 0.35, 0.7 or 1.4 in the resulting complexes. After mixing and incubating at room temperature for 10 minutes, the resulting complexes are added to 2 ml of optiMEM medium (supplied by the company GIBCO BRL) and the mixture obtained is spread on layers of ¾ confluent cells. The cells are then incubated with the complexes for 4 hours at 37° C. in a humid atmosphere containing 5 per cent $CO_2$. The medium is then replaced with 3 ml of αMEM containing 10 per cent foetal calf serum. The transfection efficiency is measured after 48 hours using luciferin as described above. The results obtained are represented on the histogram of FIG. 2, and they show that it is possible to transfect cells, even using high DNA concentrations. No significant difference was observed in the results when, instead of adding the liposomes to the DNA solution, the DNA solution was added to the solution containing the lipid formulation according to the invention.

EXAMPLE 6

A gene transfer is performed in vivo so as to induce local immune responses. 30 μg of plasmid pCMV-HA encoding haemagglutinin of the influenza virus (strain APR8) in 25 μg of physiological saline (aqueous NaCl solution at 9 g/l) are used which are added to 25 μl of deionized water containing or not cationic liposomes. One of the formulations contains only plasmid and deionized water and will be used for an assay of naked DNA transfer; one formulation contains liposomes such as those obtained in Example 1; one formulation contains liposomes such as those obtained in Example 2; the last formulation contains liposomes obtained by mixing 3β-[N-(N',N'-dimethylaminoethane)carbamoyl] cholesterol (DC chol) and dioleoylphos phatidylethanolamine (DOPE) in a 1/2 molar ratio. For each of these formulations, the quantity of liposomes used is adjusted so that in the complexes formed, the cationic amines of the liposomes represent 35 mol % of the phosphates of the plasmid DNA. The 50 μl of solution resulting from each formulation are administered intranasally (that is to say 25 μl per nostril) to Balb/c mice (5 mice per group) anaesthetized by an intraperitoneal injection of 200 μl of a ROM-PUN™ (BAYER)/IMALGENE™ (Rhône-Mérieux) mixture. 21 days after the administration of the plasmid pCMV-HA, the mice are sacrificed; their lungs and salivary glands are collected and the lymphocytes are isolated from these organs. These lymphocytes, in suspension in MEM medium containing 10% foetal calf serum, are then deposited in 96-well plates with a nitrocellulose support (multiscreen membrane HATF, millipore) previously saturated with the antigen studied (monovalent influenza vaccine HA, strain A Singapore).

After incubating for 14 hours in an atmosphere containing 5% $CO_2$ and saturated with water, the cells are lysed, the wells are rinsed and the membranes are visualized by successive washing with biotinylated anti-antibodies (mouse Anti-IgA and Anti-IgG) and then with a solution of streptavidin coupled to peroxidase and finally with a chromogen solution.

Figure 3:
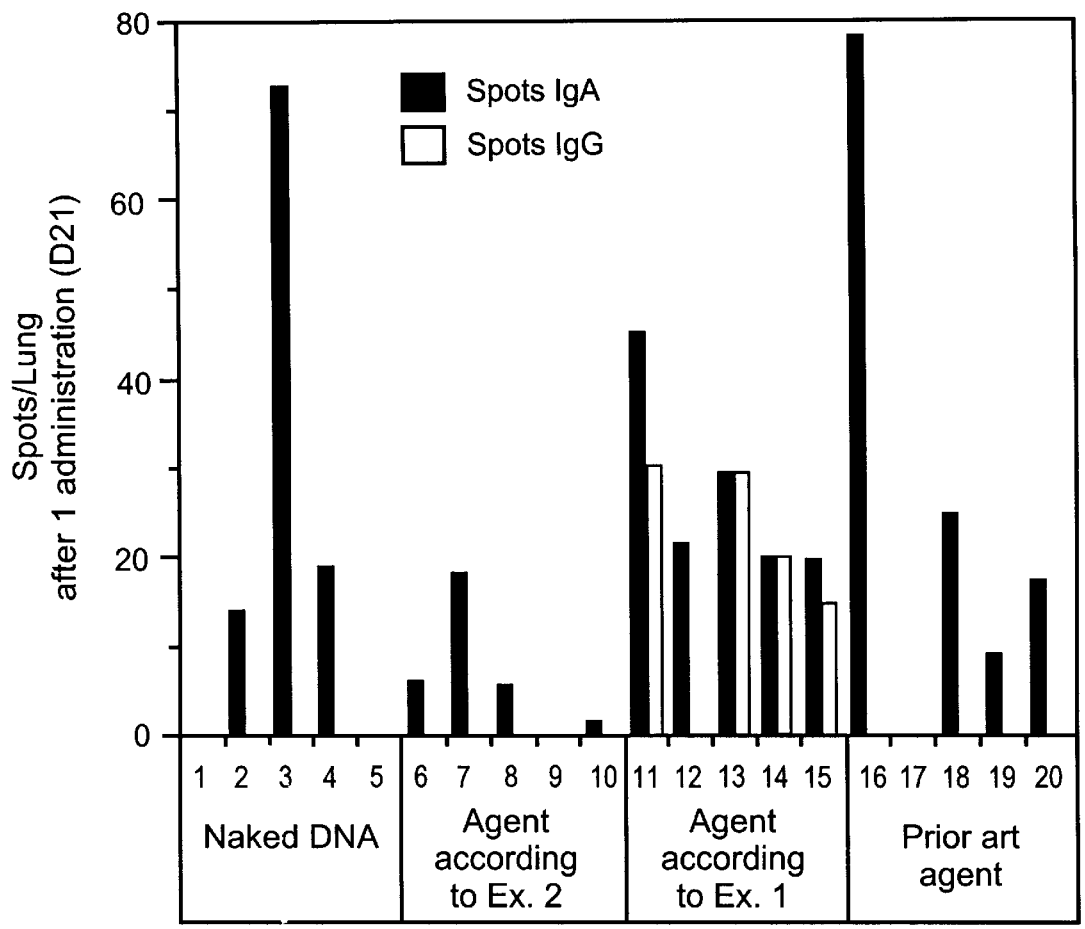
FIG. 3 illustrates the results obtained in Example 6, in mouse lungs.
Figure 4:
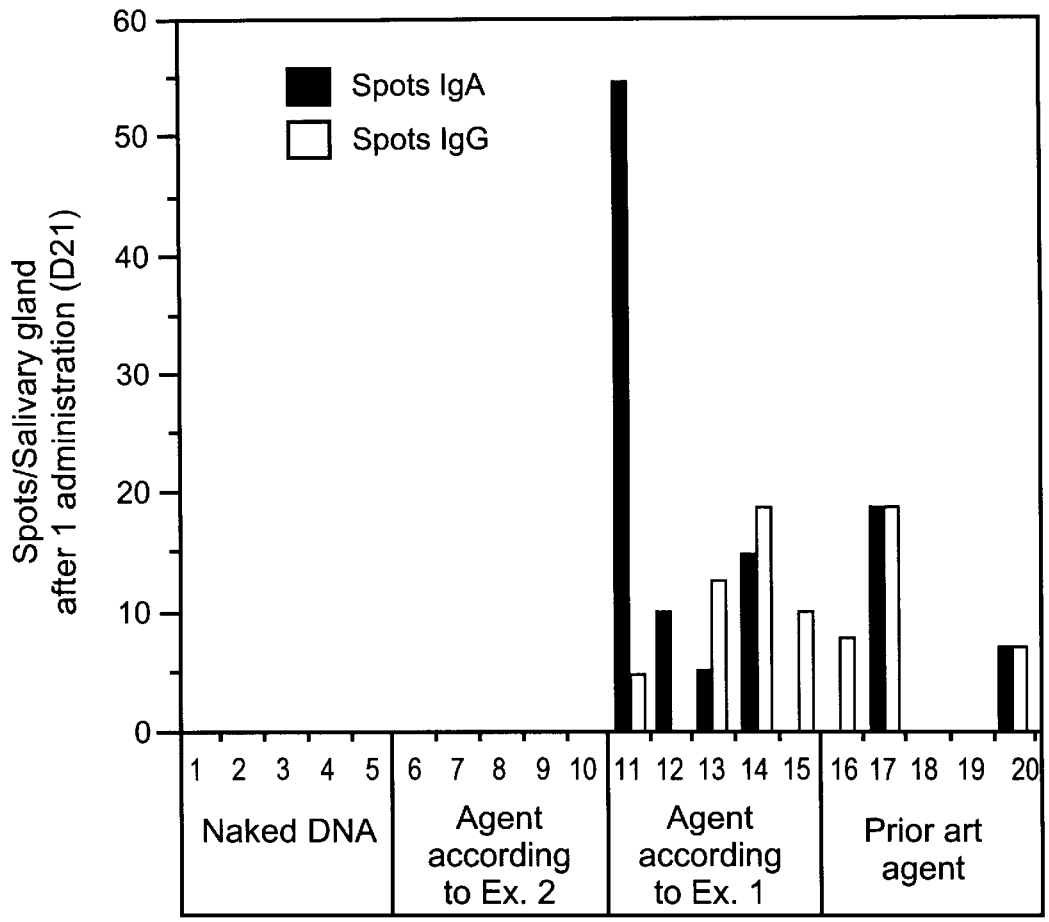
FIG. 4 illustrates the results obtained in Example 6, in mouse salivary glands.
Figure 5:
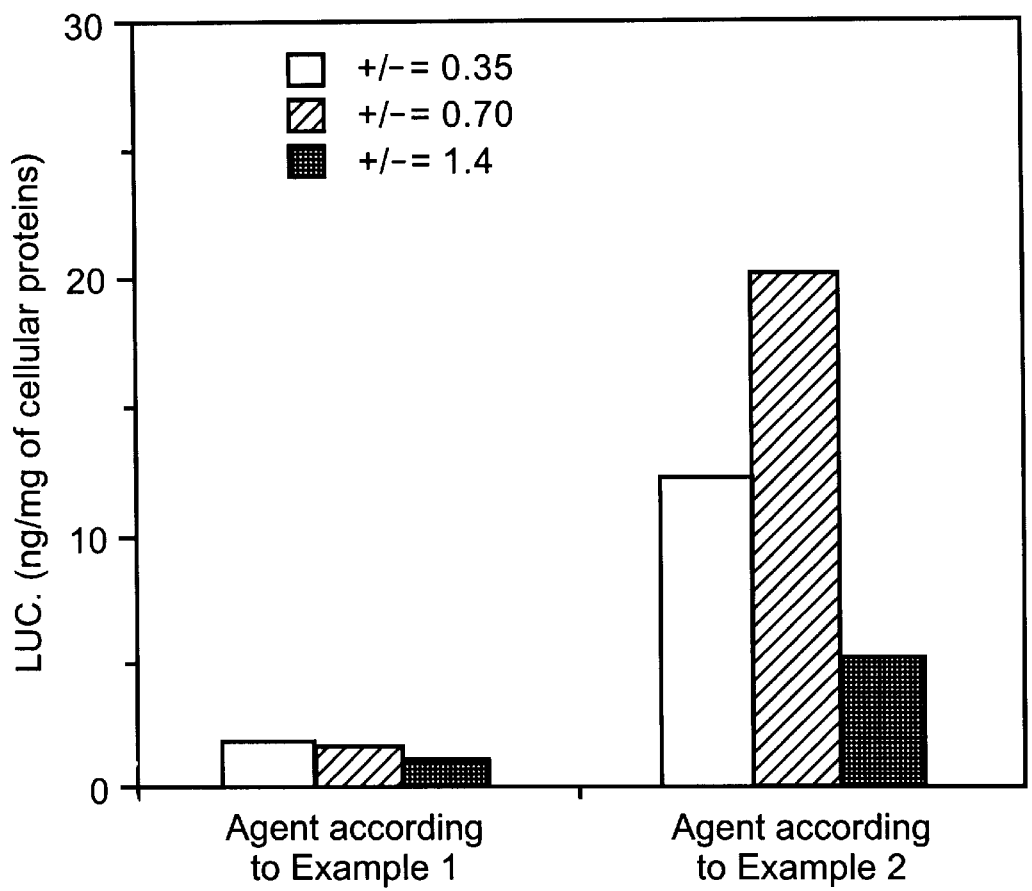
FIG. 5 illustrates the results obtained in Example 7, in mouse lungs and trachea.

The site where an antibody-secreting B lymphocyte was present appears in the form of a reddish spot which diffuses radially in the membrane of the culture well. The spots corresponding to the B lymphocytes which secrete antibodies of a given isotype (IgG or IgA) are counted under a binocular magnifying glass and their number in the lungs and in the salivary glands for each of the 5 mice of each group is plotted on the graphs of FIGS. 3 and 4. Mice 1 to 5 received the naked DNA formulation. Mice 6 to 10 received the formulation containing the transfection agent obtained according to Example 2; mice 11 to 15 received the formulation containing the transfection agent obtained in Example 1; mice 16 to 20 received the formulation containing a transfection agent of the prior art (DC chol/DOPE).

The results obtained show that a single administration of 30 μg of DNA complexed with the amphipathic compound of the invention obtained according to Example 1 makes it possible to induce B lymphocytes which secrete IgA and IgG in the lungs and salivary glands of the animals tested. This reponse is stronger and more homogeneous than that obtained respectively with naked DNA or with DNA complexed with liposomes of the prior art DC chol/DOPE.

EXAMPLE 7

A marker gene transfer in vivo is carried out in a manner identical to the transfer carried out in Example 6, but starting, this time, with 30 μg of plasmid pGL3™ (Promega, France) encoding luciferase. The formulations tested are, as in Example 6, a formulation containing liposomes such as those obtained in Example 1, a formulation containing liposomes such as those obtained in Example 2, a formulation of the prior art containing liposomes DC-Chol/DOPE. The mice tested are sacrificed 3 days after the administration of the different formulations, the lungs and trachea are collected separately and ground. The luciferase is assayed in the ground organ products by bioluminescence. A calibration curve was prepared by mixing known quantities of purified luciferase with ground lung and trachea products.

It can be observed that the best expression is obtained for the transfection carried out by means of the formulation containing the liposomes obtained in Example 1. Thus, by virtue of the transfection agent according to the invention, it is possible to carry out the transfection of the luciferase gene in vivo.

EXAMPLE 8

The adjuvant activity of a compound according to the invention is tested. To this end, a liposomal suspension is prepared from 4 mg of O, O', O"-tridodecanoyl-N-(ω-trimethylammoniododecanoyl)-tris-(hydroxymethyl) aminomethane bromide (TC-1-12 supplied by SOGO) which are dissolved in 50 μl of ethanol at 42° C. and rapidly injected with the aid of a Hamilton syringe into 1770 μl of water kept stirring at 42° C. The stirring is maintained for 2 min at 42° C. and then the liposomal suspension obtained is cooled to room temperature and there are then added dropwise to the liposomal suspension kept stirring, 230 μl of monovalent influenza vaccine NIB 16 (strain A Singapore) which contains 220 μg of haemagglutinin HA per ml. The mixture obtained is then divided into 10 doses of 200 μl each containing 5 μg of HA and 400 μg of cationic amphipathic compound. 6 female Balb/c mice, 8 to 10 weeks old, are immunized by subcutaneous injections on D0 and D21 of a dose of 200 μl of the composition prepared in the manner which has just been described. 2 weeks after the booster injection, the mice are bled at the level of the retroorbital sinus. In parallel, there are administered to 4 mice used as control 200 μl of NIB 16 vaccine diluted to 25 μg of haemagglutinin HA/ml with the aid of PBS buffer.

The serum level of antibodies IgG1 and IgG2a against the NIB 16 vaccine is then assayed by ELISA, for each of the mice tested.

The results obtained are represented in Table 4 below, and show a strong additive activity for the liposomal composition according to the invention. The increased IgG1 and IgG2a level shows that an action promoting the development both of the type TH1 lymphocytes and the type TH2 lymphocytes is present.

TABLE 4

| MOUSE | IgG1 | | IgG2a | |
| --- | --- | --- | --- | --- |
| | TITRE | GEOMETRIC MEAN | TITRE | GEOMETRIC MEAN |
| Amphipathic compound according to the invention | 55800 | | 20900 | |
| | 14690 | | 5320 | |
| | 41580 | | 4780 | |
| | 37520 | 37210 | 33990 | 16428 |
| | 50220 | | 170000 | |
| | 41330 | | 16550 | |
| Controls | <200 | | 44 | |
| | <200 | | 64 | |
| | <200 | <200 | 64 | 68 |
| | <200 | | 118 | |

What is claimed is:

1. A transfection agent comprising (a) a cationic amphipathic compound of formula I:

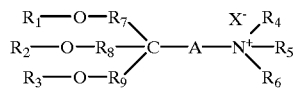

where in

A represents a single bond, an NH—R' group, or an

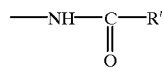

group, where —R'— is an aliphatic chain containing from 1 to 22 carbon atoms, which is linear or branched, optionally substituted, saturated or unsaturated, optionally interrupted by one or more heteroatoms O, S, N, as well as by one or more aromatic or saturated or unsaturated heterocyclic or carbocyclic radicals, $R_1$, $R_2$, $R_3$ are identical or different and each represent a higher alkyl or acyl group, $R_7$, $R_8$, $R_9$ are identical or different and each represent an alkylene radical $(CH_2)_n$ where $1 \leq n \leq 6$, $R_4$, $R_5$, $R_6$ are identical or different and each represent:
a hydrogen atom,
an alkyl, alkenyl, alkynyl or acyl radical containing from 1 to 22 carbon atoms, which is optionally substituted, optionally interrupted by one or more heteroatoms chosen from O, S, N or by one or more aromatic or saturated or unsaturated heterocyclic or carbocyclic radicals,
or alternatively, at least 2 of the groups $R_4$, $R_5$ and $R_6$ form together with the nitrogen atom to which they are linked a quinuclidino, piperidino, pyrrolidino or morpholino group,
X is a nontoxic anion; and, (b) at least one plasmid or polynucleotide.

2. The transfection agent of claim 1, wherein $R_7$, $R_8$, and $R_9$ are all identical and represent the —$CH_2$— group.

3. The transfection agent of claim 1, wherein $R_4$, $R_5$ and $R_6$ are all identical and represent the $CH_3$— group.

4. The transfection agent of claim 1, wherein $R_1$, $R_2$ and $R_3$ are all identical and represent a higher acyl group.

5. The transfection agent of claim 1, wherein A represents a group

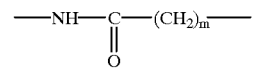

where $1 \leq m \leq 22$.

6. The transfection agent of claim 1, wherein A represents a group

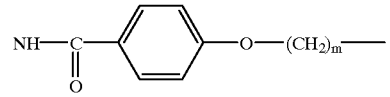

where $1 \leq m \leq 22$.

7. The transfection agent of claim 1, further comprising a neutral lipid.

8. The transfection agent of claim 7, wherein said neutral lipid is dioleoylphosphatidylethanolamine.

9. The transfection agent of claim 7, wherein the cationic amphipathic compound of formula I/neutral lipid molar ratio is between 9/1 and 1/9.

10. A method of transfecting eukaryotic cells comprising mixing at least one plasmid or polynucleotide with a cationic amphipathic compound of formula I:

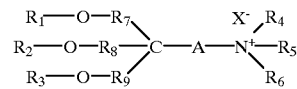

wherein

A represents a single bond, an NH—R' group, or an

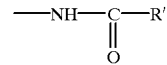

group, where —R'— is an aliphatic chain containing from 1 to 22 carbon atoms, which is linear or branched, optionally substituted, saturated or unsaturated, optionally interrupted by one or more heteroatoms O, S, N, as well as by one or more aromatic or saturated or unsaturated heterocyclic or carbocyclic radicals, $R_1$, $R_2$, $R_3$ are identical or different and each represent a higher alkyl or acyl group, $R_7$, $R_8$, $R_9$ are identical or different and each represent an alkylene radical $(CH_2)_n$ where $1 \leq n \leq 6$, $R_4$, $R_5$, $R_6$ are identical or different and each represent:
a hydrogen atom,
an alkyl, alkenyl, alkynyl or acyl radical containing from 1 to 22 carbon atoms, which is optionally substituted, optionally interrupted by one or more heteroatoms chosen from O, S, N or by one or more aromatic or saturated or unsaturated heterocyclic or carbocyclic radicals,
or alternatively, at least 2 of the groups $R_4$, $R_5$, and $R_6$ form together with the nitrogen atom to which they are linked a quinuclidino, piperidino, pyrrolidino or morpholino group; and, bringing the mixture thus obtained into contact with the cells to be transfected.

11. A vaccine composition comprising (a) a cationic amphipathic compound of

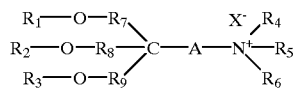

wherein

A represents a single bond, an NH—R' group, or an

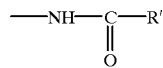

group, where —R'— is an aliphatic chain containing from 1 to 22 carbon atoms, which is linear or branched, optionally substituted, saturated or unsaturated, optionally interrupted by one or more heteroatoms O, S, N, as well as by one or more aromatic or saturated or unsaturated heterocyclic or carbocyclic radicals, $R_1$, $R_2$, $R_3$ are identical or different and each represent a higher alkyl or acyl group, $R_7$, $R_8$, $R_9$ are identical or different and each represent an alkylene radical $((CH_2)_n$ where $1 \leq n \leq 6$, $R_4$, $R_5$, $R_6$ are identical or different and each represent:
   a hydrogen atom,
   an alkyl, alkenyl, alkynyl or acyl radical containing from 1 to 22 carbon atoms, which is optionally substituted, optionally interrupted by one or more heteroatoms chosen from O, S, N or by one or more aromatic or saturated or unsaturated heterocyclic or carbocyclic radicals, or alternatively, at least 2 of the groups $R_4$, $R_5$ and $R_6$ form together with the nitrogen atom to which they are linked a quinuclidino, piperidino, pyrrolidino or morpholino group, X is a nontoxic anion; and, (b) at least one plasmid or polynucleotide.

12. A method for vaccinating a patient in need thereof comprising administering to said patient a therapeutically effective amount of the vaccine of claim 11.

13. A pharmaceutical composition comprising (a) a cationic amphipathic compound of formula I:

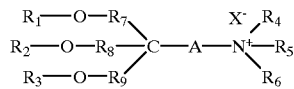

wherein

A represents a single bond, an NH—R' group, or an

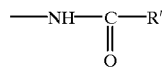

group where —R'— is an aliphatic chain containing from 1 to 22 carbon atoms, is linear or branched, optionally substituted, saturated or unsaturated, optionally interrupted by one or more heteroatoms O, S, N, as well as by one or more aromatic or saturated or unsaturated heterocyclic or carbocyclic radicals, $R_1$, $R_2$, $R_3$ are identical or different and each represent a higher alkyl or acyl group, $R_7$, $R_8$, $R_9$ are identical or different and each represent an alkylene radical $(CH_2)_n$ where $1 \leq n \leq 6$, $R_4$, $R_5$, $R_6$ are identical or different and each represent:
   a hydrogen atom,
   an alkyl, alkenyl, alkynyl or acyl radical containing from 1 to 22 carbon atoms, which is optionally substituted, optionally interrupted by one or more heteroatoms chosen from O, S, N or by one or more aromatic or saturated or unsaturated heterocyclic or carbocyclic radicals,
   or alternatively, at least 2 of the groups $R_4$, $R_5$ and $R_6$ form together with the nitrogen atom to which they are linked a quinuclidino, piperidino, pyrrolidino or morpholino group, X is a nontoxic anion; and, (b) at least one plasmid or polynucleotide.

14. A gene therapy method comprising administering to a patient in need thereof a therapeutically effective amount of the composition of claim 13.

15. A vaccine composition comprising an adjuvant and an antigen; said adjuvant comprising a cationic amphipathic compound of formula I:

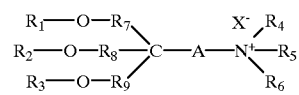

wherein

A represents a single bond, an NH—R' group, or an

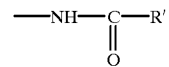

group, where —R'— is an aliphatic chain containing from 1 to 22 carbon atoms, which is linear or branched, optionally substituted, saturated or unsaturated, optionally interrupted by one or more heteroatoms O, S, N, as well as by one or more aromatic or saturated or unsaturated heterocyclic or carbocyclic radicals, $R_1$, $R_2$, $R_3$ are identical or different and each represent a higher alkyl or acyl group, $R_7$, $R_8$, $R_8$ are identical or different and each represent an alkylene radical $(CH_2)_n$ where $1 \leq n \leq 6$, $R_4$, $R_5$, $R_6$ are identical or different and each represent:
   a hydrogen atom,
   an alkyl, alkenyl, alkynyl or acyl radical containing from 1 to 22 carbon atoms, which is optionally substituted, optionally interrupted by one or more heteroatoms chosen from O, S, N or by one or more aromatic or saturated or unsaturated heterocyclic or carbocyclic radicals,
   or alternatively, at least 2 of the groups $R_4$, $R_5$ and $R_6$ form together with the nitrogen atom to which they are linked a quinuclidino, piperidino, pyrrolidino or morpholino group, X is a nontoxic anion.

16. A method for vaccinating a patient in need thereof comprising administering to said patient a therapeutically effective amount of the vaccine of claim 15.

17. A pharmaceutical composition comprising (a) a cationic amphipathic compound of formula I:

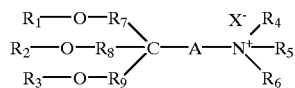

wherein

A represents a single bond, an NH—R' group, or an

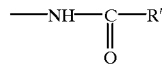

group, where —R'— is an aliphatic chain containing from 1 to 22 carbon atoms, which is linear or branched, optionally substituted, saturated or unsaturated, optionally interrupted by one or more heteroatoms O, S, N, as well as by one or more aromatic or saturated or unsaturated heterocyclic or carbocyclic radicals, $R_1$, $R_2$, $R_3$ are identical or different and each represent a higher alkyl or acyl group, $R_7$, $R_8$, $R_9$ are identical or different and each represent an alkylene radical $(CH_2)_n$ where $1 \leq n \leq 6$, $R_4$, $R_5$, $R_6$ are identical or different and each represent:
a hydrogen atom,
an alkyl, alkenyl, alkynyl or acyl radical containing from 1 to 22 carbon atoms, which is optionally substituted, optionally interrupted by one or more heteroatoms chosen from O, S, N or by one or more aromatic or saturated or unsaturated heterocyclic or carbocyclic radicals,
or alternatively, at least 2 of the groups $R_4$, $R_5$ and $R_6$ form together with the nitrogen atom to which they are linked a quinuclidino, piperidino, pyrrolidino or morpholino group, X is a nontoxic anion; and, an antigen.

* * * * *